(12) United States Patent
Chang et al.

(10) Patent No.: US 9,315,544 B2
(45) Date of Patent: *Apr. 19, 2016

(54) METHOD OF TREATING EOSINOPHILIA BY ADMINISTERING AN IMMUNOMODULATING PEPTIDE

(71) Applicant: National Tsing Hua University, Hsinchu (TW)

(72) Inventors: Margaret Dah-Tsyr Chang, Hsinchu (TW); Lin-Shien Fu, Taichung (TW); Shun-Lung Fang, Hsinchu (TW)

(73) Assignee: National Tsing Hua University, Hsinchu (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/022,795

(22) Filed: Sep. 10, 2013

(65) Prior Publication Data

US 2014/0072574 A1 Mar. 13, 2014

Related U.S. Application Data

(60) Provisional application No. 61/698,835, filed on Sep. 10, 2012.

(51) Int. Cl.
| | |
|---|---|
| A61K 38/19 | (2006.01) |
| C07K 7/06 | (2006.01) |
| A61K 38/08 | (2006.01) |
| A61K 39/395 | (2006.01) |
| C07K 14/52 | (2006.01) |
| C12N 9/22 | (2006.01) |

(52) U.S. Cl.
CPC . *C07K 7/06* (2013.01); *A61K 38/08* (2013.01); *A61K 39/3955* (2013.01); *C07K 14/523* (2013.01); *C12N 9/22* (2013.01); *C12Y 301/27* (2013.01)

(58) Field of Classification Search
CPC ........................................ A61K 38/00
USPC ........................................ 424/85.1
See application file for complete search history.

(56) References Cited

U.S. PATENT DOCUMENTS

| 6,426,070 B1* | 7/2002 | Rosenberg et al. ........ 424/94.61 |
| 2006/0183114 A1* | 8/2006 | Hogbom et al. .................. 435/6 |
| 2012/0214730 A1* | 8/2012 | Chang et al. .................... 514/1.7 |

OTHER PUBLICATIONS

Niimi et al. Clinical Experimental Allergy. 1998; 28(2): 233-240.*
Fiorini et al. Serum ECP and MPO are increased during exacerbations of chronic bronchitis with airway obstruction. Biomedicine and Pharmacotherapy. 2000; 54(5): 247-278.*
Motojima et al. Toxicity of eosinophil cationic proteins for guinea pig tracheal epithelium in vitro. American Review of Respiratory Disease. 1989; 139(3): 801-805.*
Maeda et al. Growth inhibition of mammalian cells by eosinophil cationic protein. European Journal of Biochemistry. 2002; 269: 307-316.*
Marc E. Rothenberg, "Eosinophilia", The New England Journal of Medicine, May 28, 1998, vol. 338, pp. 1592-1600.
Singh V et al., "Approach to a case of Eosinophilia",Ind J Aerospace Med, 2009, vol. 53(2), pp. 58-64.
Ayalew Tefferi et al., "Hypereosinophilic Syndrome and Clonal Eosinophilia: Point-of-Care Diagnostic Algorithm and Treatment Update", Mayo Clinic Proceedings, Feb. 2010, vol. 85(2), pp. 158-164.
Rankin Sara M. et al., "Eotaxin and eosinophil recruitment: implications for human disease", Molecular Medicine Today, Jan. 2000 (vol. 6), pp. 20-27.
Sosnoski Donna M. et al., "Changes in Cytokines of the Bone Microenvironment during Breast Cancer Metastasis", (2012) International Journal of Breast Cancer, vol. 2012, Article ID 160265, 9 pages.
Holgate, Stephen T., "Innate and adaptive immune responses in asthma", Nature Medicine, May 2012, vol. 18, pp. 673-683.
Szefler, Staney J. et al., "Asthma outcomes: Biomarkers" (2012) J. Allergy Clin. Immunol, vol. 129, pp. S9-23.
Stevens, W.H.M. et al., "Allergen-induced Oxygen Radical Release from Bronchoalveolar Lavage Cells and Airway Hyperresponsiveness in Dogs", Am J Respir Crit Care Med, 1995, vol. 151, pp. 1526-1531.
Berger, A., "Science commentary: Th1 and Th2 responses: what are they?", BMJ, Aug. 12, 2000, vol. 321, p. 424.
Besnard, Anne-Gaelle et al., "Inflammasome-IL-1-Th17 response in allergic lung inflammation" Journal of Molecular Cell Biology, 2012, vol. 4, pp. 3-10.
Cox, Linda. "Accelerated immunotherapy schedules: review of efficacy and safety", Ann Allergy Asthma Immunol. 2006, vol. 97, pp. 126-137.
Giembycz Ma, et al, "Pharmacology of the Eosinophil", Pharmacological Reviews,1999, vol. 51, No. 2pp. 213-340.
Gleich, Gerald J. "Mechanisms of eosinophil-associated inflammation", J Allergy Clin Immunol, Apr. 2000, vol. 105, pp. 651-663.
Rosenberg Helene F. et al, "Molecular Cloning of a Cytotoxin and Helminthotoxin with Ribonuclease Activity", J Exp Med, Jul. 1989, vol. 170, pp. 163-176.
Chang Kun-Che et al, "TNF-α Mediates Eosinophil Cationic Protein-induced Apoptosis in BEAS-2B Cells", BMC Cell Biology 2010, vol. 11, No. 6, 14 pages.
Boix, Ester et al., "Kinetic and Product Distribution Analysis of Human Eosinophil Cationic Protein Indicates a Subsite Arrangement That Favors Exonuclease-type Activity", Journal of Biological Chemistry, 1999, vol. 274, pp. 15605-15614.
Fan Tan-Chi et al., "A Heparan Sulfate-Facilitated and Raft-Dependent Macropinocytosis of Eosinophil Cationic Protein", Traffic, 2007, vol. 8, pp. 1778-1795.
Fan Tan-Chi et al., "Characterization of Molecular Interactions between Eosinophil Cationic Protein and Heparin", The Journal of Biological Chemistry, Sep. 12, 2008, vol. 283, No. 37, pp. 25468-25474.

(Continued)

*Primary Examiner* — Prema Mertz
(74) *Attorney, Agent, or Firm* — WPAT, P.C.; Anthony King

(57) ABSTRACT

A method of treating or preventing inflammatory related diseases in a subject in need thereof comprising administering to said subject a pharmaceutically effective amount of a composition comprising an immune modulating polypeptide of SEQ ID NO: 1 is provided. A method for inhibiting cancer metastasis or growth of tumor in a subject in need thereof, comprising administering to the subject a pharmaceutically effective amount of a composition comprising an immune modulating polypeptide of SEQ ID NO: 1 is also provided.

11 Claims, 12 Drawing Sheets

(56) References Cited

OTHER PUBLICATIONS

Fang, Shun-Lung et al. "A Novel Cell-Penetrating Peptide Derived from Human Eosinophil Cationic Protein", PLoS One, 2013, vol. 8, e57318.

Lien, Pei-Chun et al. "In Silico Prediction and In Vitro Characterization of Multifunctional Human RNase3", BioMed Research International, 2013, vol. 2013, Article ID 170398, 12 pages.

Maeda Takashi et al, "Growth inhibition of mammalian cells by eosinophil cationic protein", Eur J Biochem, 2002, vol. 269, pp. 307-316.

Chang, Ya-Jen et al. "Innate lymphoid cells mediate influenza-induced airway hyper-reactivity independently of adaptive immunity", Nature Immunology, Jul. 2011, vol. 12, No. 7, pp. 631-638.

Ford, Jean G. et al, "IL-13 and IFN-g: Interactions in Lung Inflammation", The Journal of Immunology, 2001, vol. 167, pp. 1769-1777.

Padrid Philip et al, "Persistent Airway Hyperresponsiveness and Histologic Alterations after Chronic Antigen Challenge in Cats", Am J Respir Crit Care Med, 1995, vol. 151, pp. 184-189.

Mukherjee Sumanta et al. "IL-17-Induced Pulmonary Pathogenesis during Respiratory Viral Infection and Exacerbation of Allergic Disease", The American Journal of Pathology, Jul. 2011, vol. 179, No. 1, pp. 248-258.

Doe Camille et al. "Expression of the T Helper 17-Associated Cytokines IL-17A and IL-17F in Asthma and COPD", Chest, 2010, vol. 138, No. 5, pp. 1140-1147.

* cited by examiner

METHOD OF TREATING EOSINOPHILIA BY ADMINISTERING AN IMMUNOMODULATING PEPTIDE

FIELD OF THE INVENTION

This invention relates to a method of treating or preventing inflammatory related diseases using a composition that modulating immune response, blocking and reducing generation of symptom. Additionally, this invention also relates to a method of using a composition that changes gene expression as indicated as immunomodulatory effect.

DESCRIPTION OF PRIOR ART

Effective immune response is necessary to clear pathogenic microorganisms and malignant cells. An excessive immune response produces clinical symptoms that can be life threatening. Immunomodulation restore ability to resolve inflammation, which in turn should allow a return of tissue integrity. Eosinophilia is a common finding in premature infants during the neonatal period, and its incidence increases with immaturity. Previous studies have reported eosinophilia in association with numerous conditions, such as the establishment of an anabolic state, drug reactions, response to foreign antigens, chronic lung disease, erythropoietin treatment, total parenteral nutrition, and infections (Marc E. Rothenberg, (1998) NEJM, 338:1592-1600). Among allergic or vasculitis causes of secondary eosinophilia, eosinophilic lung diseases are noteworthy and include acute and chronic eosinophilic pneumonia, allergic bronchopulmonary aspergillosis, allergic angiitis and granulomatosis (Churg-Strauss syndrome—eosinophilia, asthma, systemic vasculitis, and lung infiltrates) (Singh V et al., (2009) IJASM, 53: 58-64, Ayalew Tefferi et al., (2010) Mayo Clin Proc., 85: 158-164).

CCL-11 (CC-type chemokine ligand-11) induces aggregation of eosinophil, an elevation in their intracellular calcium levels and respiratory burst activity. Furthermore, CCL-11 enhances the adhesion of eosinophil to endothelial cells. Chronic inflammatory diseases of the nose and sinuses, including nasal polyposis, allergic rhinitis and both allergic and non-allergic sinusitis, are all characterized by an eosinophil-rich inflammatory infiltrate. In all these disease states, upregulation of CCL-11 protein has been detected (Rankin S M, et al., (2000) Mol Med Today, 6:20-27). CCL-11 mRNA is markedly upregulated in the lesions of patients with inflammatory bowel disease and could explain the mechanism of eosinophil recruitment in diseases such as ulcerative colitis and Crohn's disease (Rankin S M, et al., (2000) Mol Med Today, 6:20-27). In Hodgkin's disease, levels of CCL-11 protein have been shown to correlate directly with extent of tissue eosinophilia (Rankin S M, et al., (2000) Mol Med Today, 6:20-27). Thus, evidence to date suggests that there is a potential role for CCL-11 in a variety of diseases that are characterized by a tissue eosinophilia. In addition to its chemoattractant effect, CCL-11 can stimulate release of eosinophil and their progenitors from bone marrow, resulting in rapid blood eosinophilia. CCL-11 promotes differentiation of bone marrow haematopoietic progenitors towards myeloid lineage during inflammation and embryogenesis (Rankin S M, et al., (2000) Mol Med. Today., 6:20-27). Beside eosinophilia, CCL11 may enable metastatic cancer cells to colonize and thrive in cancer environment. In mouse model of skeletal breast cancer metastasis, vascular endothelial growth factor (VEGF) and CCL11 levels were significantly higher in femurs of cancer cell-inoculated compared to sham-inoculated mice (Sosnoski D M. et al., (2012) Int J Breast Cancer 2012:160265). CCL-11 is therefore prime targets for therapeutic intervention in diseases characterized by an eosinophilia and cancer metastasis.

Asthma, brochiitis, allergic bronchitis, bronchial asthma, emphysema, chronic obstructive pulmonary disease (COPD) and lung fibrosis are known collectively as pulmonary diseases. These diseases are characterized as airway obstruct ion, especially of small airways, associated with symptoms of asthma, brochiitis and emphysema. Airway obstruction is defined as an increased resistance to airflow during forced expiration, especially in asthma (Stephen T H (2012) Nat. Med, 18: 673-683). Asthma is a reversible obstructive pulmonary disorder caused by an airway hyper-responsiveness to specific or non-specific stimuli. Asthma is a chronic airway inflammation mediated by many cells such as epithelial cell, macrophage, neutrophil, eosinophil, mast cell, T cell and B cell (Stanely J. S. et al., (2012) J. Allergy Clin. Immunol 129:S9-23), among which eosinophil, mast cell and T helper type 2 (Th2) cell are most important in allergic inflammation. Pathology in asthma is caused by inappropriate responses to inhaled allergens, and characterized by reversible obstruction of airway hyperresponsiveness (AHR), airway inflammation, and imbalance of Th2-mediated or Th1-mediated cytokines (Stevens, W. H., et al., (1995) Am J Respir Crit Care Med, 151: 1526-31). Cytokines secreted by Th1 cell include tumor necrosis factor-$\beta$ (TNF-$\beta$) and interferon-$\gamma$ (INF-$\gamma$) which are responsible for killing intracellular parasites and for perpetuating autoimmune responses; Th2 cell secreted cytokines include interleukin-4 (IL-4), IL-5 and IL-13 which play critical roles in allergic diseases and have been targeted for immune modulation by monoclonal antibodies (Berger A., (2000) BMJ, 321: 424). Hence many factors play critical roles in allergic inflammation (Besnard, A. G., et al., (2012) J Mol Cell Biol, 4: 3-10).

Current asthma therapies, such as inhaled corticosteroids, $\beta_2$-agonists, M cholinergic receptor antagonists, or anti-leukotrienes, are directed at symptom relief, reduction or neutralization of effector molecules and inflammatory mediators. These therapies are effective for acute disease and for relieving symptoms. However, they have limited long-term salutary effects. Conventional allergen immunotherapy, while having long-term and impressive efficacy, requires multiple injections over several years and is associated with frequent failure and occasional immunoglobulin E (IgE)-mediated adverse events (Cox, L. (2006) Ann Allergy Asthma Immunol 97, 126-137). Therefore, an alternative, more effective and long-lasting therapeutic approach for asthma has been focused on the development of vaccine strategies that alter the underlying immune response and convert detrimental allergic responses to protective immune responses, thereby modifying the course of the disease.

Several proteins housed in eosinophil granules are suggested to contribute to the remodeling and AHR associated severe asthma, including eosinophil peroxidise, major basic protein, eosinophil derived neurotoxin (EDN), and eosinophil cationic protein (ECP). ECP contributes to elimination of invading microbes, such as parasite and virus (Giembycz M A, et al, (1999) Pharmacol Rev 51:213-340). In addition, together with other proteins secreted from eosinophils, ECP is thought to cause damage of airway, a common feature of airway allergic inflammation in asthma (Gleich G H. (2000) J Allergy Clin Immunol, 105: 651-663). Among these proteins, ECP and EDN are members of pancreatic ribonuclease A family and have ribonuclease activity, which might damage epithelium and neuron leading to airway remodeling and vagal dysfunction (Rosenberg H F, et al, (1989) J Exp Med 170: 163-176). ECP also plays a critical role in inhibiting cell proliferation in mammalian cell lines (Chang K. C., et al, (2010) *BMC Cell Biol.* 11: 6). The mechanism underlying cytotoxic property of ECP is unclear because its ribonuclease activity is much lower than EDN (Boix, E., et al, (1999) *J. Biol. Chem.* 274: 15605-15614). It has been hypothesized that ECP cytotoxicity is due to destabilization of lipid membranes of target cells, and degree of cytotoxicity is dependent on cellular concentration. The contribution of proteoglycans in ECP interaction with mammalian cells suggests that ECP binds to carbohydrates at cell surface (Chang K. C., et al, (2010) *BMC Cell Biol.* 11: 6) and presents a high affinity for glycosaminoglycan (GAG) structures, in particular, heparin. Cytotoxicity of ECP was severely reduced toward cell lines with heparin sulfate (HS) deficiency (Fan T. C., et al, (2007) *Traffic* 8: 1778-1795).

A sequential segment of ECP has been identified as a heparin-binding motif (Fan, T. C., et al. (2008) *J Biol Chem* 283: 25468-25474, U.S. Pat. No. 7,595,374) and treated asthma by reducing cytotoxicity of ECP in bronchial epithelial cells (U.S. Pat. No. 8,399,416). Cytokine modulatory peptide (CMP) a 10-amino acid peptide containing major heparin-binding motif of ECP, delivered molecule into cells with no cytotoxic effect on bronchial epithelial cell (Fang, S. l., et al. (2013) *PLoS One,* 8: e57318, U.S. Pat. No. 8,372,951). Interestingly, CMP displays multiple properties such as heparin/heparan sulfate binding, lipid binding and cellular binding activities (Lien, P. C., et al. (2013) *Biomed Res Int,* 2013: 170398). It could delivers small fluorescent compound, recombinant protein, and peptidomimetic drug into cells, and selectively targets epithelial organs in BALB/c mouse in vivo (Fang, S. l., et al. (2013) *PLoS One,* 8: e57318, U.S. Pat. No. 8,372,951). Its heparin-binding and cell-penetrating characters facilitate alleviating inflammatory related diseases by modulating cytokine. Therefore, this invention demonstrates effects on mite-induced airway allergic inflammation in BALB/c mouse.

SUMMARY OF THE INVENTION

Figure 1A:
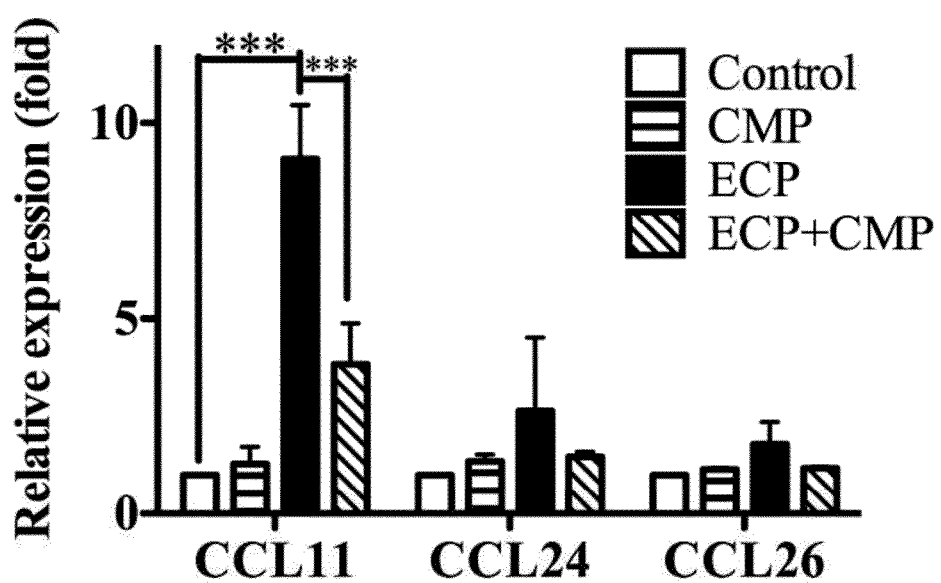
FIG. 1A-1B illustrates immunomodulatory effect of CMP on transcription of cytokine. Beas-2B cells were starved with serum free medium for 24 h, followed by stimulation with refold 5 μM ECP or 5 μM CMP or co-treatment with 5 μM ECP and 5 μM CMP at 37° C. for (A) 6 h and (B) 12 h, respectively. The mRNA quantities of CCL11, CCL24 and CCL26 were determined by real-time PCR. Beas-2B cells without protein treatment were used as control. These data were expressed as relative fold with mock-treated set as one. The data represented at least three independent experiments and the error bar was shown as standard deviation (SD).

The present invention provides a method for treating or preventing inflammatory related disease in a subject in need thereof by modulating CCL11 expression in the subject, comprising administering to the subject a pharmaceutically effective amount of a composition comprising an immune modulating polypeptide of SEQ ID NO: 1

The present invention also provides a method for inhibiting cancer metastasis or growth of tumor in a subject in need thereof, comprising administering to the subject a pharmaceutically effective amount of a composition comprising an immune modulating polypeptide of SEQ ID NO: 1.

DETAILED DESCRIPTION OF THE INVENTION

The detailed description provided below in connection with the appended drawings is intended as a description of the present examples and is not intended to represent the only forms in which the present example is constructed or utilized. The description sets forth the functions of the examples and the sequence of steps for constructing and operating the examples. However, the same or equivalent functions and sequences may be accomplished by different examples.

The terms "a", "an", and "the" as used herein are defined to mean "one or more" and include plural referents unless the context clearly dictates otherwise.

The present invention provides a method for treating or preventing inflammatory related disease in a subject in need thereof by modulating CCL11 expression in the subject, comprising administering to the subject a pharmaceutically effective amount of a composition comprising an immune modulating polypeptide of SEQ ID NO: 1 (NYRWRCKNQN). The subject of the present invention is mammal having established a cancer, an autoimmune disorder, an airway inflammation, inflammatory disorders, skin disorders or a disease caused by a pathogen. The example of pathogen includes, but not limited to, bacteria, viruses, mold, dander, funguses, dust mites, storage mites, stinging insects, mosquitoes/midges, cockroaches, or animal The example of autoimmune disorder includes, but not limited to, multiple sclerosis, asthma, arthritis, myasthenia gravis, arthritis, lupus erythematosus, pemhigus, psoriasis, colitis, rejection of transplanted organs, rejection of xenotransplants or immuno-deficiency diseases. The example of cancer includes, but not limited to, colon cancer, rectal cancer, stomach cancer, pancreatic cancer, lung cancer, metastatic pancreatic cancer, ovarian cancer or breast cancer. The example of airway inflammation is asthma, bronchitis, allergic bronchitis, bronchial asthma, emphysema, COPD, or lung fibrosis. The route of administration is selected from sublingual, transdermal, topical, mucosal, inhalation, intranasal, aerosol, intraocular, intratracheal, dermal patch or eye drop.

Preferably, the composition reduces inflammation, airway obstruction, bronchial spasms, airway hyperreactivity, histopathological inflammation score, goblet cells hyperplasia, IgE levels, chemokine levels, inflammatory cytokine levels or TLR4 pathway in the subject.

In another preferred embodiment, the composition decreases airway resistance in the subject.

In another preferred embodiment, the composition reduces leukocyte (macrophage, basophil, neutrophil, eosinophil, segment or lymphocyte) recruitment or chemokine (CCL-11, CCL-26, CXCL-12) levels or inflammatory cytokine (IL-4, IL-5, IL-6, IL-8, IL-13, IL-18 or IL-17A/F) levels in the subject.

In another preferred embodiment, the subject is human having established airway inflammation or human that has experienced previous pulmonic symptoms.

In another preferred embodiment, the composition reduces severity of asthma attack, airway obstruction, bronchial spasms, airway hyperreactivity, histopathological inflammation score, goblet cells hyperplasia or IgE levels in the subject.

In the other preferred embodiment, the method of the present invention further comprises administering the composition in combination with a agent selected from the group consisting of steroids, anti-Ig E antibodies, anti-IL-4 antibodies, anti-IL-5 antibodies, leukotriene inhibitors, lipoxyoenase inhibitors, IL-13 antagonists, cytokine release inhibitors, anti-histamines and histamine release inhibitors.

The present invention also provides a method for inhibiting cancer metastasis or growth of tumor in a subject in need thereof, comprising administering to the subject a pharmaceutically effective amount of a composition comprising an immune modulating polypeptide of SEQ ID NO: 1. Preferably, the cancer metastasis is lung cancer metastasis. In another preferred embodiment, the subject is mammal.

EXAMPLES

Example 1

Immuomodulatory Effect of CMP in Transcription of Epithelial Cells

Experimental Protocol
Cytokine mRNA Expression Analysis by Quantitative Real-Time PCR For inflammatory cytokine expression analysis, Beas-2B cells were stimulated with three different conditions: 1) 5 μM ECP, 2) 5 μM CMP and 3) co-incubated with 5 μM ECP and 5 μM CMP at 37° C. for 6 and 12 h. After incubation, total RNAs were extracted with RNA TRIzol reagent (Invitrogen, Inc) and reverse transcribed with MoMLV-reverse transcriptase (Promega, Madison, Wis.). SYBR Green-based quantitative real-time PCR will be used to quantify the gene of interest, relative expression ratios of genes of interest were normalized to glyceraldehyde-3-phosphate dehydrogenase (GAPDH) transcripts. Changes in cytokine expression were measured by quantitative real-time PCR (qRT-PCR) employing the StepOne™ amplification and detection system (Life Technologies Corporation). Data were analyzed by application of the StepOne™ quantification program software (version 2.22, Life Technologies Corporation) and expressed as means±S.D. Significance analysis was carried out by a two-sample unequal variance t-test with two-tailed distribution (post test). Significance was set as $P<0.05$.

Figure 1B:
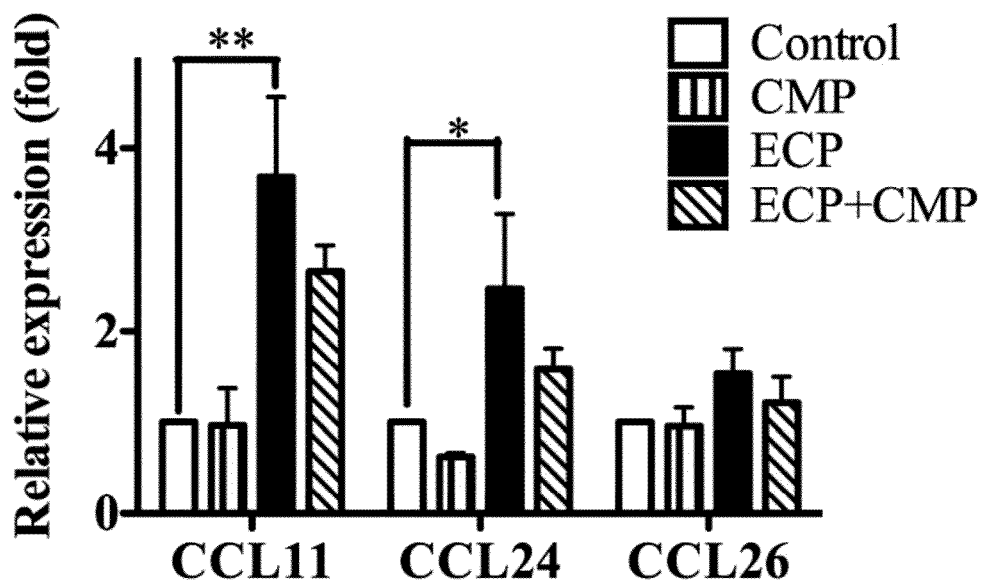

ECP, the best known marker protein of asthma, is involved in triggering cytokine expression in bronchial epithelial cells. Real-time PCR analysis was carried out to quantify expression levels of indicated cytokines upon treatment with recombinant ECP in the presence and absence of CMP Bronchial epithelial Beas-2B cells were separately cultured in serum-free medium in the presence of 5 μM ECP, 5 μM CMP and both 5 μM ECP and 5 μM CMP for 6 and 12 h to monitor cytokine and chemokine gene modulation using real-time quantitative PCR. Untreated Beas-2B cells incubated at the same condition for 6 h and 12 h were used as negative controls. Here variation of gene expression levels of chemokines including CCL11, CCL24 and CCL26 was analyzed. Notably, CCL11 and CCL26 gene expression level increased 9- and 2-fold, respectively, in ECP treated Beas-2B cells at 6 h (FIG. 1A), and CCL11 gene expression level increased 2.8-fold, respectively, in ECP treated Beas-2B cells at 12 h (FIG. 1B). Interestingly, CMP alone had no effect in Beas-2B cells after treatment for 6 and 12 h. Furthermore, co-treatment with both ECP and CMP for 6 h resulted in a significant reduction in ECP-induced gene expression of CCL11 in Beas-2B cells, suggesting that CMP might interfere CCL11-mediated immune response induced by ECP in bronchial epithelial cells, and further reduced asthmatic symptoms.

Example 2

Immuomodulatory Effect of CMP on Translation of CCL11

Experimental Protocol

Human CCL11 Enzyme-Link Immunosorbent Assay (ELISA) Kit

CCL11 ELISA kit (R&D) is an in vitro enzyme-linked immunosorbent assay for quantitative determination of human CCL11 concentration in cell culture supernatants. This assay employed an antibody specific for human CCL11 coated on a 96-well plate. The wells were incubated with 50 μL standard or sample for 2.5 hours at room temperature. After washing with 1× wash solution five times, 200 μL of CCL11 conjugate were added into each wells for 1 h. After washing, 100 μL TMB One-Step Substrate Reagent were added into each wells at room temperature for 30 minutes. 50 μL of Stop Solution were added into each wells and read at 450 nm by spectrophotometer immediately. Limit of detection in the assay was 5 pg/mL.

Figure 2:
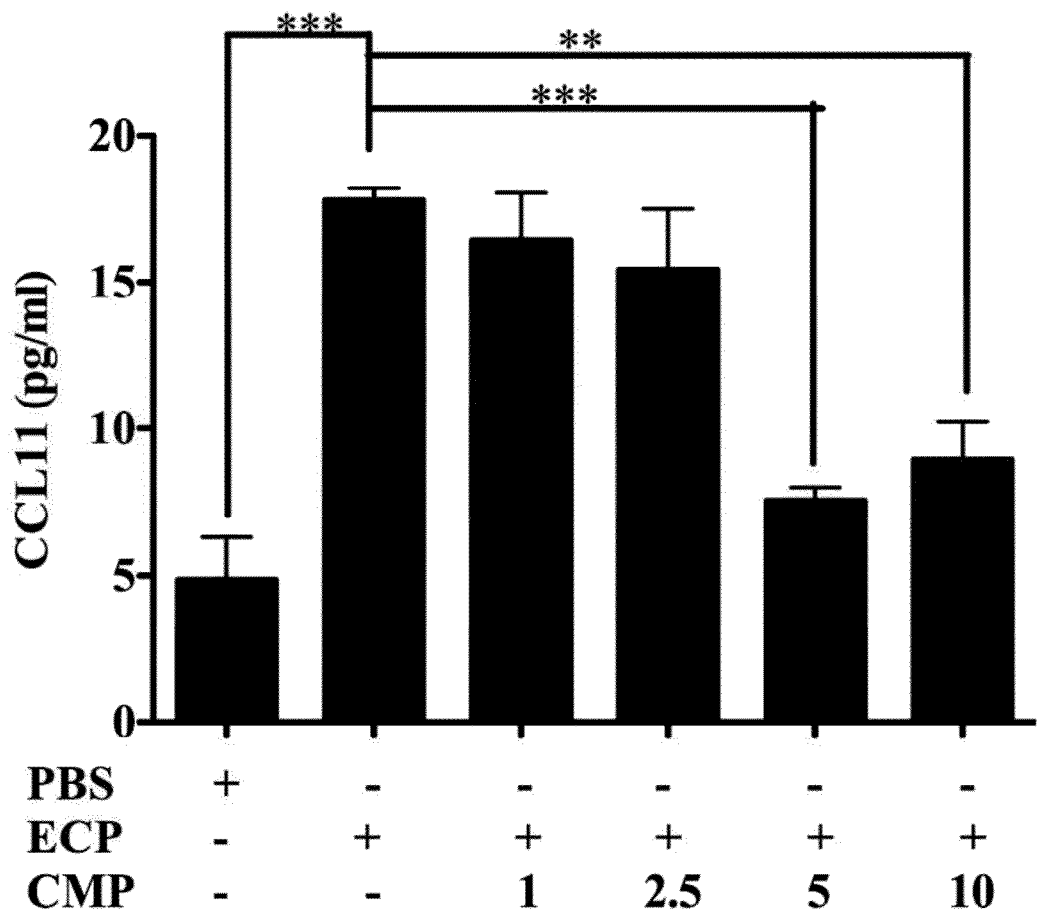
FIG. 2 illustrates CCL11 expression in CMP and ECP co-treated Beas-2B cells. Beas-2B cells were starved with serum free medium for 24 h, followed by stimulation with ECP (column 2). Cells were stimulated with PBS as negative control (column 1) and ECP in the absence of CMP (column 2) or presence of 1 μM (column 3), 2.5 μM (column 4), 5 μM (column 5), 10 μM (column 6) CMP at 37° C. for 24 h. CCL11 protein level was determined by ELISA kit employing CCL11 antibody. The data represented mean±SD (standard deviation) of at least three independent experiments. *, $p<0.001$; , $p<0.01$

To investigate whether CMP influenced ECP-mediated CCL11 expression, Beas-2B cells were separately stimulated with 5 μM ECP in the absence of CMP and in the presence of 1 μM, 2.5 μM, 5 μM and 10 μM CMP at 37° C. for 24 h. The results demonstrated that 17.8 pg/mL CCL11 release was induced upon treatment with 5 μM ECP (FIG. 2). Combination of 5 μM ECP and 1 or 2.5 μM CMP did not reduce ECP-mediated CCL11 production. Interestingly, up regulation of CCL11 induced by ECP was significantly reduced to 7.55 pg/mL and 8.94 pg/mL upon co-treatment with respectively 5 and 10 μM CMP (FIG. 2). These data indicated that rescue of CCL11 production stimulated by ECP might not be comprised by all CPPs and what is a specific signal streaming involved in CMP function.

Figure 3:
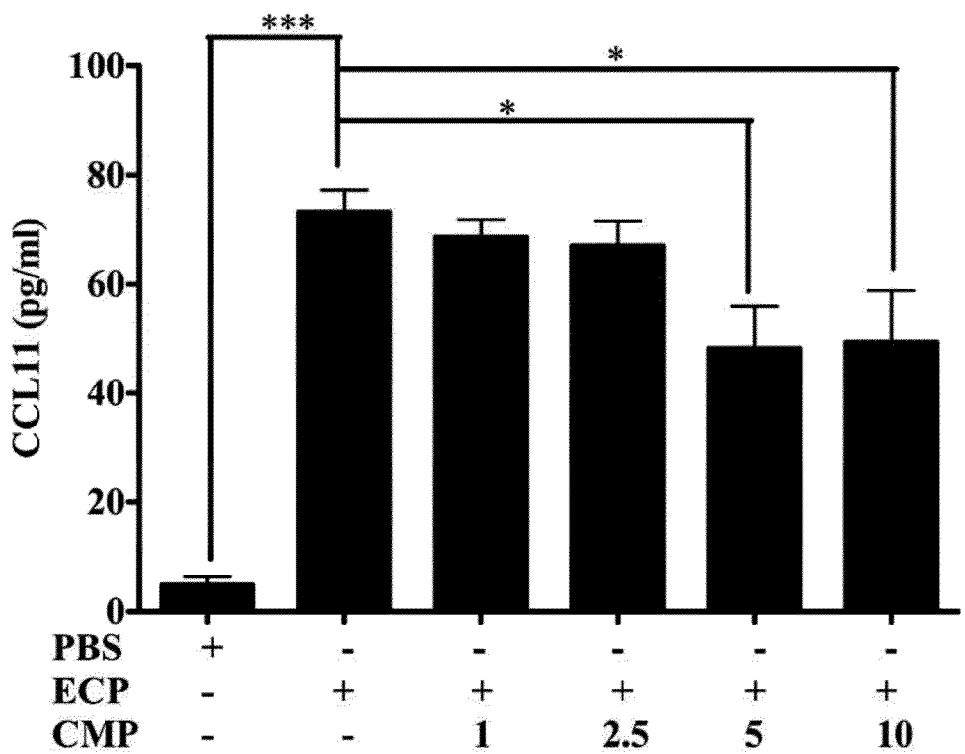
FIG. 3 illustrates CCL11 expression in CMP and IL-4 co-treated Beas-2B cells. Beas-2B cells were starved with serum free medium for 24 h, followed by stimulation with PBS (column 1) or 10 ng/mL IL-4 (column 2-7). Cells were stimulated with 10 ng/mL IL-4 in the absence (column 1) or presence of 1 μM (column 3), 2.5 μM (column 4), 5 μM (column 5) and 10 μM (column 6) CMP at 37° C. for 24 h. CCL11 protein level was determined by ELISA kit employing CCL11 antibody. The data represented mean±SD (standard deviation) of at least three independent experiments. ***, $p<0.001$ (Stimulation with IL-4 compared with PBS treated Beas-2B cells). *, $p<0.05$ (Stimulation with indicated concentrations of CMP compared with IL-4 treated Beas-2B cells).

To further investigate whether CMP influenced CCL11 production from other stimulation in Beas-2B cells, serum-deprived Beas-2B cells were stimulated with 10 ng/mL IL-4, a dominant cytokine regulating CCL11, alone or in the presence of CMP at concentrations 1, 2.5, 5 and 10 μM at 37° C. for 24 h. The results demonstrated that 73.2 pg/mL CCL11 release was induced upon treatment with 10 ng/mL IL-4 (FIG. 3). Combination of 10 ng/mL IL-4 with 1 or 2.5 μM CMP did not reduce CCL11 production induced by IL-4 (FIG. 3). While combination of 10 ng/mL IL-4 with 5 or 10 μM CMP led to reduced release of CCL11 to 48.1 pg/mL and 30.2 pg/mL, respectively (FIG. 3). These results revealed that both refold ECP and IL-4 induced chemokine CCL11 expression in Beas-2B cells, and addition of 5 and 10 μM CMP, but not TAT[47-57] could down-regulate CCL11 expression induced by refold ECP and IL-4.

Example 3

Significant Reduction Airway Hyperreactivity In Vivo

Experimental Protocol

Figure 4:
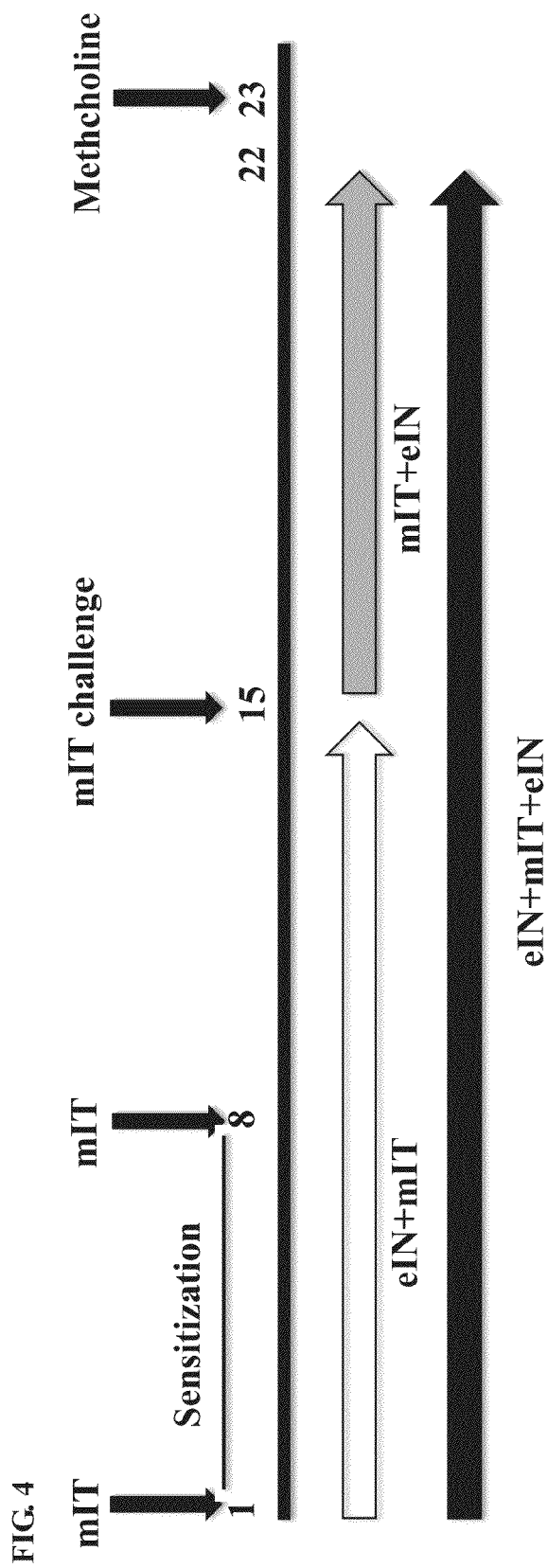
FIG. 4 illustrates experimental design. All groups except control group were immunized with mite crude extract allergen on days 1 and 8, then mite crude extract allergen intratracheally on day 15 in all mite treated group, BALB/c mouse were divided into six groups (1) control group (PBS), (2) mites delivered intratracheally (mIT, mite on day 15) alone, (3) CMP intranasal (eIN, CMP on days 1 to 22) alone, (4) preventive-treatment group (eIN+mIT, CMP on days 1 to 14, mite on day 15) (5) therapy-treatment group (mIT+eIN, mite on day 15, CMP on days 15 to 22), and (6) preventive- and therapeutic-treatment group (eIN+mIT+eIN, CMP on days 1 to 22, mite on day 15).

Mice were divided into six groups: 1) control (n=10), 2) mite crude extract allergen delivered intratracheally (mIT) alone (n=10), 3) CMP intranasal (eIN) alone (n=12), 4) preventive-treatment group (eIN+mIT; n=12), 5) therapeutic-treatment group (mIT+eIN; n=12), and 6) preventive- and therapeutic-treatment group (eIN+mIT+eIN; n=18) (FIG. 4). All groups receiving mIT were immunized with mite crude extract allergen on days 1 and 8 and then given mite crude extract allergen intratracheally on day 15. The cIN and eIN+mIT+eIN groups received cIN from days 1 to 22, the cIN+mIT group received eIN from days 1 to 15 (before mIT), and the mIT+eIN group received eIN from days 15 (post-mIT) to 22. All mice were sacrificed on day 23. The animal use protocol was reviewed and approved by Institutional Animal Care and Use Committee (IACUC Approval No: La-95279).

Measurement of Pause Enhancement (Penh)

Airway responsiveness was measured in mouse on day 22 (i.e., 1 hour after the last challenge) in conscious, spontaneously breathing mouse using a whole-body plethysmography system (Buxco, Wilmington, N.C., USA) as described before (Maeda T, et al, *Eur J Biochem* 2002, 269, 307-316). Briefly, mice were individually placed in the chamber and allowed to settle for 3-5 min. The chamber-pressure-time wave was continuously measured via a transducer connected to a computer data acquisition system. After a baseline Penh reading for >3 min, mice were serially exposed to increasing concentrations of nebulized methacholine (MCh) (0, 6.25, 12.5, and 25 mg/ml; Sigma, St Louis, Mo., USA) in PBS for 1 min by inhalation. Penh values, which are measured as changes in enhanced pause, tidal volume, and breathing frequency (breaths/minute) for the first 3 min after the end of MCh nebulization, were averaged and used to compare responses among all six-treatment groups.

Figure 5:
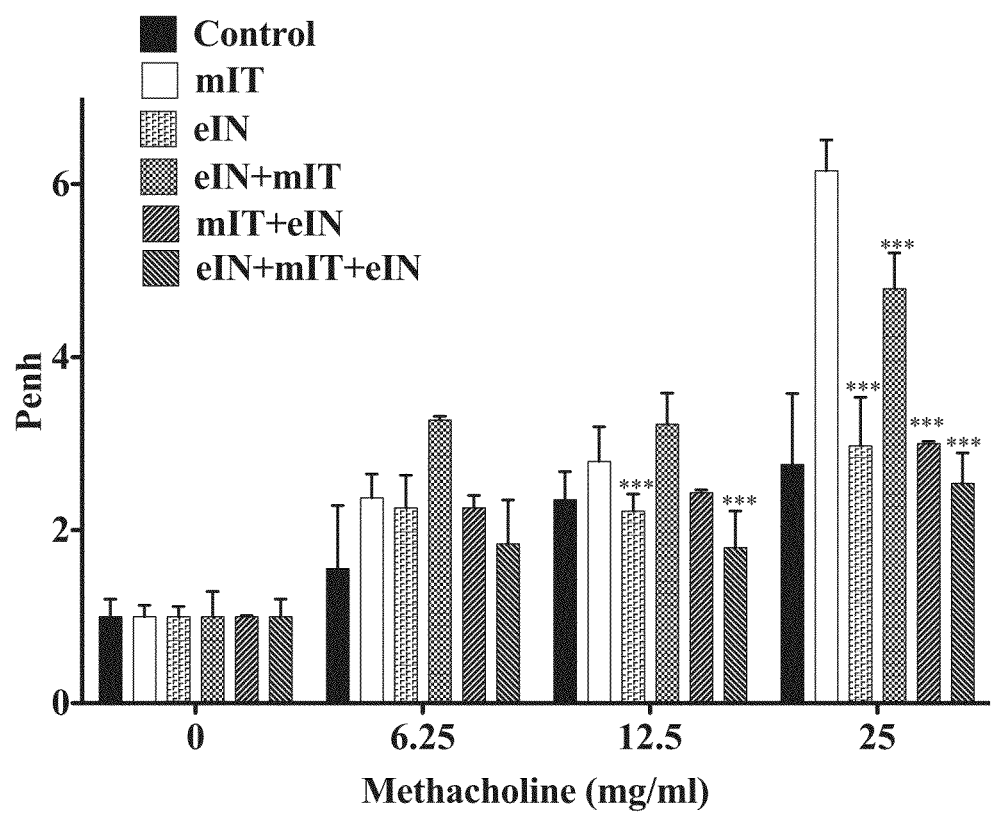
FIG. 5 illustrates inhibitory effect of CMP on mite-induced airway hyperresponsiveness. The effect of methacholine (MCh) on pause enhancement (Penh) in mouse exposed to CMP in the presence and absence of mite proteins. Penh was measured in all six treatment groups after stimulation with 6.25, 12.5, or 25 mg/ml MCh for 1 min. The values were presented as a ratio with respect to the baseline Penh (before MCh stimulation) for each group. Each result was expressed as the mean±S.D., n=4. , $P<0.01$. *, $P<0.001$.

Bronchial spasm, a chief characteristic of asthma, induces airway obstruction and airway hyperreactivity (AHR) and then decreases air flow (Stephen T. H. (2012) *Nat. Med,* 18: 673-683). AHR is a clinical feature of asthma and is often in proportion to the underlying severity of disease (Chang, Y. J. et al. (2011) *Nat. Immunol.* 12: 631-638). To evaluate the effects of CMP on mite-induced asthma, AHR was evaluated by measuring changes of Penh in all experimental groups of mice. The treatment of eIN+mIT, mIT+eIN and eIN+mIT+eIN could significantly decrease AHR in mice, as assessed by their response to increase the dose of inhaled methacholine (FIG. 5). The mIT group showed a much higher Penh/baseline ratio change after stimulation with 12.5 and 25 mg/ml MCh than control, eIN+mIT+eIN and eIN groups. The eIN+mIT and mIT+eIN groups showed lower stimulation than mite group treated with 25 mg/ml MCh, but not with 12.5 mg/ml MCh. These results demonstrated that CMP could reduce airway obstruction, bronchial spasms, and increased air flow in allergen-induced AHR. In conclusion, CMP could exert its preventive and therapeutic effect in asthma mouse model.

Example 4

Histopathologic Changes in Lung Tissues

Histopathological Analysis

The formalin-fixed lung sections stained with hematoxylin and eosin (H&E) were assigned a unit value for alveolar, peri-bronchiolar, and total inflammation by computing the means of three independent scores for three randomly selected fields. Each section was independently and blindly interpreted by two physicians and was followed a previous scoring system for airway inflammation (Ford J G, et al, (2001) *J Immunol* 167: 1769-77). For evaluating the hyperplasia goblet cells, medium-sized airways were assessed in sections stained with periodic acid-Schiff (PAS) stain. Two reviewers independently and randomly scored 10 fields of each slide. Each lung was assigned a unit by computing the mean of the numerical scores. The numerical scores for the abundance of PAS-positive goblet cells (Padrid P, et al, (1995) *Am J Respir Crit. Care Med* 151: 184-9) in each airway were determined as follows: 0, 5% goblet cells; 1, 5-25%; 2, 25-50%; 3, 50-75%; 4, 75%.

Figure 6A:
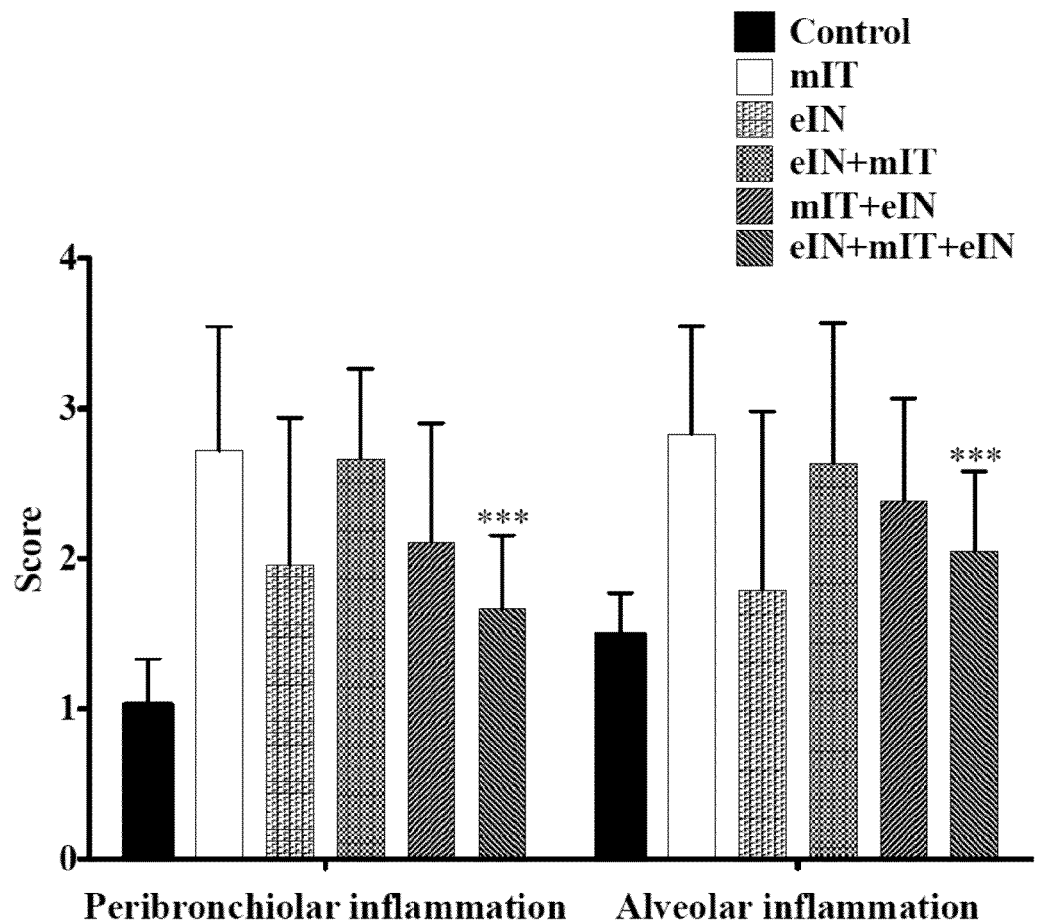
FIG. 6A-6B illustrates inhibitory effect of CMP on influx of inflammatory cells. Immunohistological analysis of representative sections of lung tissue, obtained from different treatment groups after allergen challenge, was performed. Histological sections were stained with haematoxylin and eosin (H&E) for general morphology and cellular infiltration or periodic acid-Schiff (PAS) stain for goblet cell hyperplasia and mucin production. (A) Scores for peri-bronchiolar, alveolar inflammation and (B) PAS were determined based on the histological sections. Each result was expressed as the mean±S.D., n=4. ***, $P<0.001$.
Figure 6B:
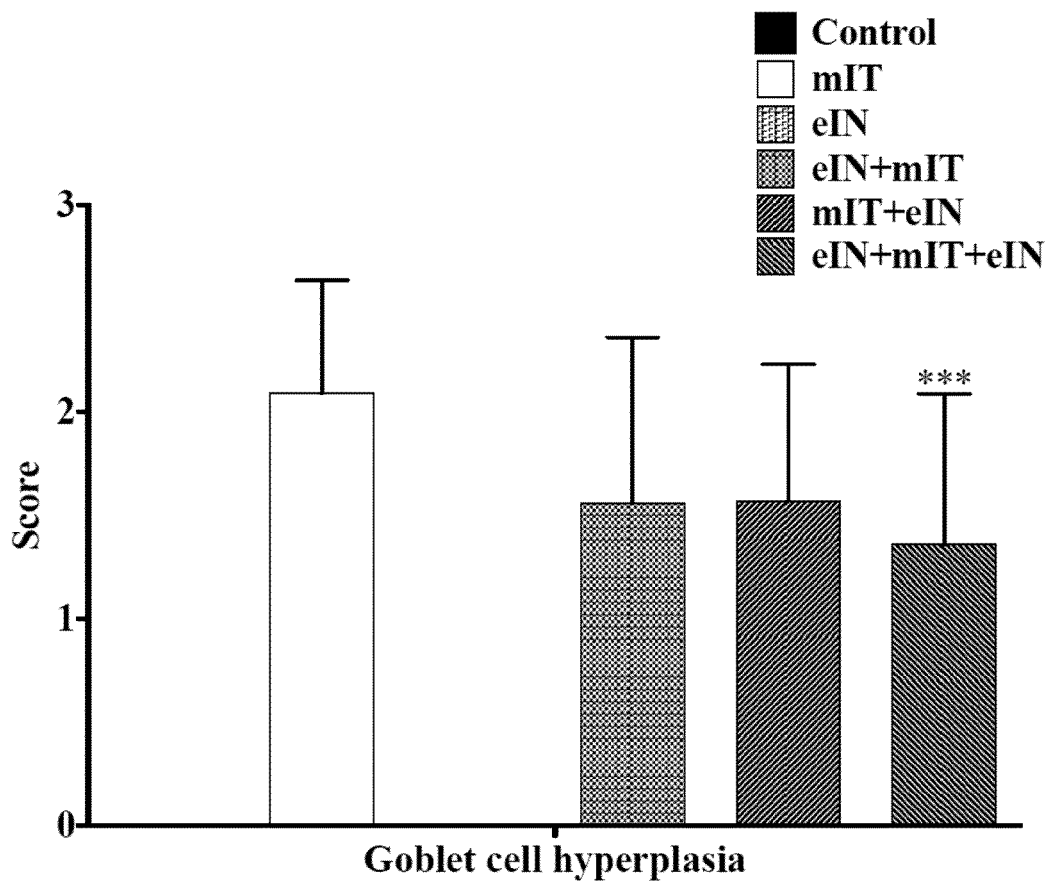

To determine whether suppression of AHR could represent more complete pathology, lung histological sections were compared among the six groups of mice. The scores of peri-bronchiolar and alveolar inflammation were shown in FIG. 6A. Layers of cell infiltration were found in the peri-bronchial and alveolar area in the lungs of the mIT group. There were significantly lower peri-bronchiolar and alveolar scores in eIN+mIT+eIN group than in the mIT group. The scores of goblet cell hyperplasia were shown in FIG. 6B. The group eIN+mIT+eIN had lower score than mIT group. Take together; eIN+mIT+eIN had a more potently suppressive effect on peribronchiolar, alveolar inflammation and goblet cells hyperplasia than eIN+mIT and mIT+eIN group. The evidence from animal studies could prove that CMP indeed decreased the effect of airway inflammation and goblet cells hyperplasia to allergens stimuli.

Example 5

Suppression of Cell Recruitment In Vivo

Bronchoalveolar Lavage Fluid and Measurement of Cell Count

The trachea was exposed and cannulated. Two washings, each consisting of 1.0 ml of phosphate-buffered saline, were introduced into the lungs via the cannula and withdrawn to collect the cells. Bronchoalveolar lavage fluid (BALF) from each wash was placed in polypropylene tubes on ice. The collected BALF was then centrifuged at 300×g for 7 min at 4° C. After supernatant removal, cells were resuspended in 1.0 ml of phosphate-buffered saline (pH 7.4). Total cell numbers were counted on a hemocytometer, and $1-5 \times 10^3$ cells were spun onto glass microscope slides (cytospin, Shandon Scientific, Cheshire, UK). The cell slides were air dried for 24 h, fixed, and stained with Wright stain. Differential cell counts of at least 300 cells per slide were made according to morphological criteria. The number of cells recovered was calculated and expressed as absolute cell numbers.

Figure 7:
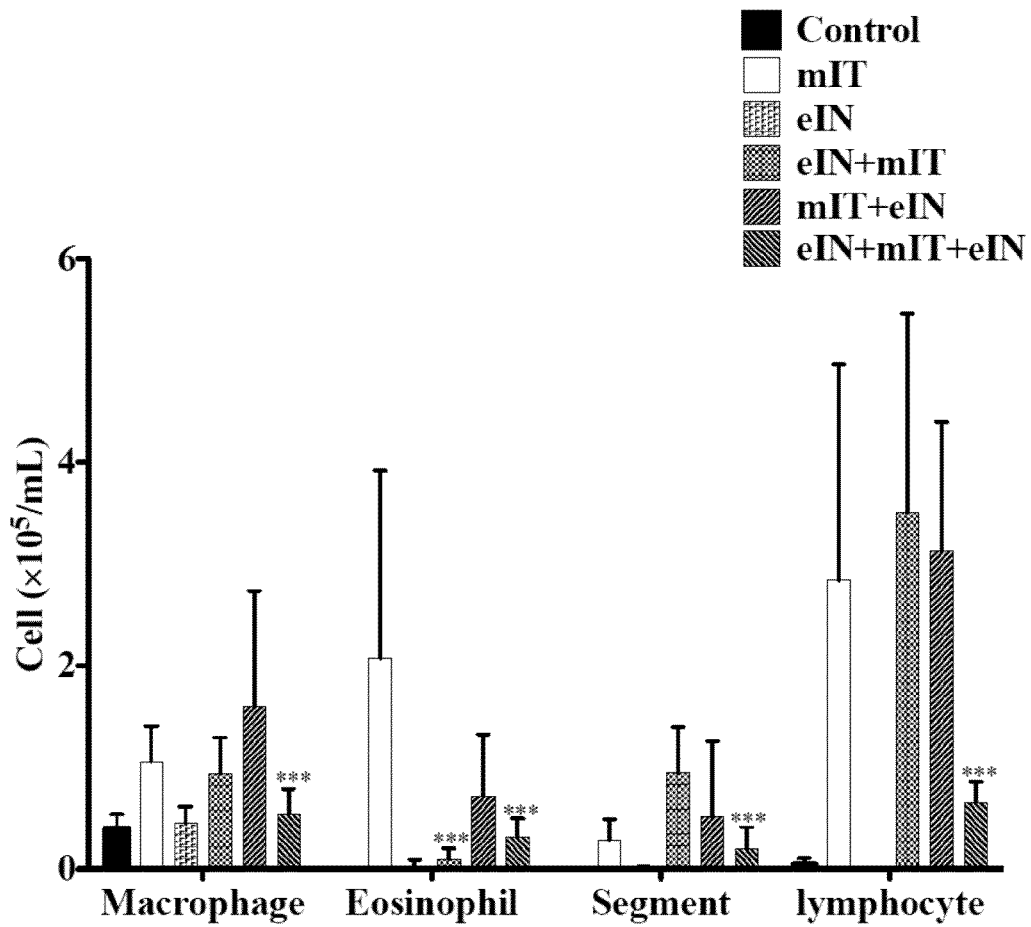
FIG. 7 illustrates inhibitory effect of CMP on cell response in bronchoalveolar lavage fluid (BALF). BALF were collected from all experimental groups of mice. Cell populations were identified on air-dried cytocentrifuged smears after staining with Diff-Quuick stain. Differential cell counts were performed on a minimum of 300 cells to identify macrophages, eosinophils, segment or lymphocytes. Data represent one of three independent experiments. Each result was expressed as the mean±S.D., n=4. ***, $P<0.001$.

To identify the extent of inflammatory cell recruitment into the airways under allergen challenge circumstance, the amount of inflammatory cell were measured in BALF. As shown in FIG. 7, eIN+mIT+eIN group had lower macrophage, eosinophil and lymphocyte counts than mIT group. The eIN+mIT had lower eosinophil count than mIT group. A significant decrease took place in cell recruitment into the airways after treatment with CMP, indicating that CMP inhibited airway inflammation in asthma mice.

Example 6

Suppression of Mite-Specific Serum IgE Levels

Measurement of Serum DerP-Specific IgE

Blood samples were collected from mouse tails (day 18) and from the inferior vena cava after finishing treatment (day 23) and serum were separated. Mite protein (5 μg) was coated on the plated at 4° C. overnight. Then, the sera from day 18 and day 23 were added on coated plated. Standard anti-IgE antibody was purchased from B. D. (San Diego, Calif., USA). The levels of serum mite-specific IgE were measured by enzyme-linked immunosorbent assay (ELISA).

Figure 8:
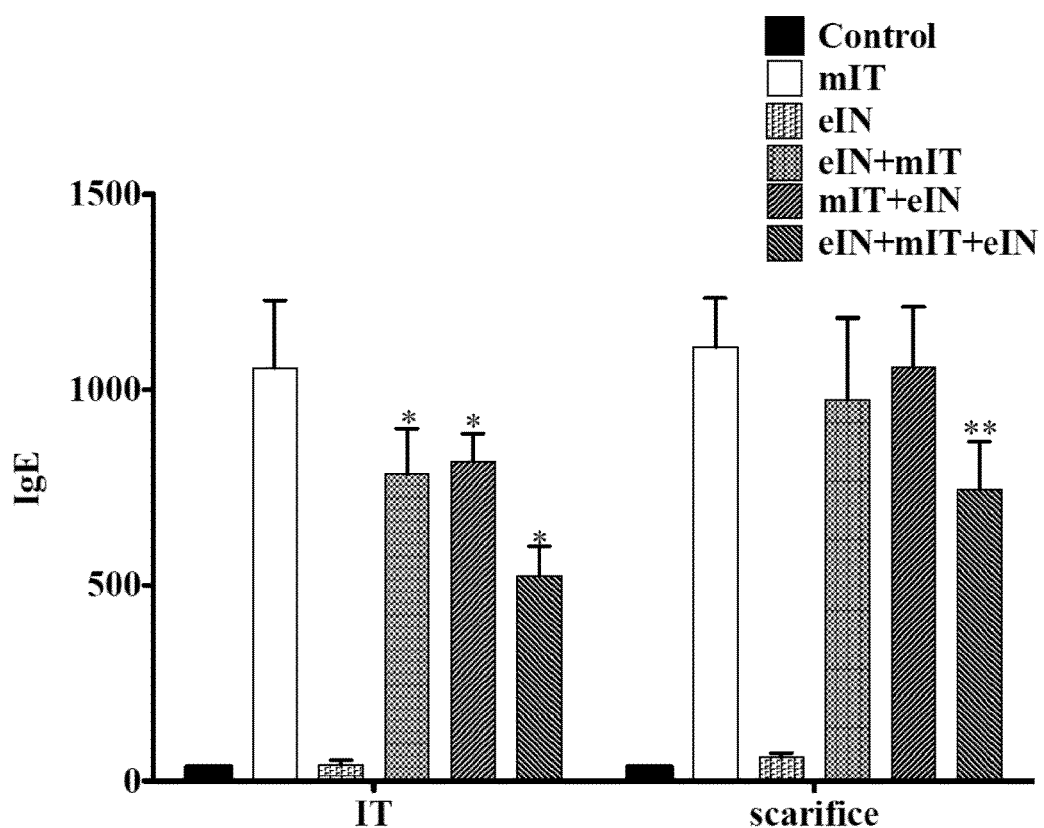
FIG. 8 illustrates inhibitory effect of CMP on serum IgE level. Blood samples were collected from mouse tails (day 18) and from the inferior vena cava 24 hours after the final intranasal treatment (day 23) and serum were separated. Levels of serum Derp-specific IgE were measured by enzyme-linked immunosorbent assay (ELISA). Each result was expressed as the mean±S.D., n=4. *, $P<0.05$, **, $P<0.01$.

To further analyze therapeutic effect of CMP on mite sensitization, serum mite-specific IgE levels in mice were measured from all six treatment groups. The sera were obtained on day 18 from tails and day 23 from inferior vena cava (IVC) (FIG. 8). The mIT group had a higher IgE reading than did the eIN+mIT, mIT+eIN, and eIN+mIT+eIN groups on day 18. The eIN+mIT+eIN groups had much lower IgE level than did the mIT group on day 23. CMP reduced the key molecule, specific IgE, strongly providing a mechanistic explanation for the down-regulation of airway inflammation in asthma mouse.

Example 7

Suppression of T Helper Type 2 Cytokines in Lung Protein Extract

Preparation of Lung Tissue Supernatant

The left lung was homogenized in 1.0 mL of cold phosphate buffered saline and preserved in ice bath before use. Lung homogenates were centrifuged at 20,000×g for 5 min at 4° C. Lung tissue homogenate supernatants were then diluted in PBS to a final protein concentration of 500 μg/ml and stored at −80° C.

Cytokine Analysis with ELISA

Levels of cytokines from lung protein extract were measured by ELISA. BD OptEIA™ Set Mouse IL-5, IL-10, IL-13, IFN-γ, and transforming growth factor-β (TGF-β) kits (BD Bioscience, San Jose, Calif., USA) and DuoSet mouse eotaxin, IL-17A/F, Vascular endothelial growth factor (VEGF), and matrix metallopeptidase 9 (MMP 9) kits (R&D, Minneapolis, Minn., USA) were used. The microplates were read at 450 nm with an ELISA reader (Thermo Labsystems, Waltham, Mass., USA).

Figure 9:
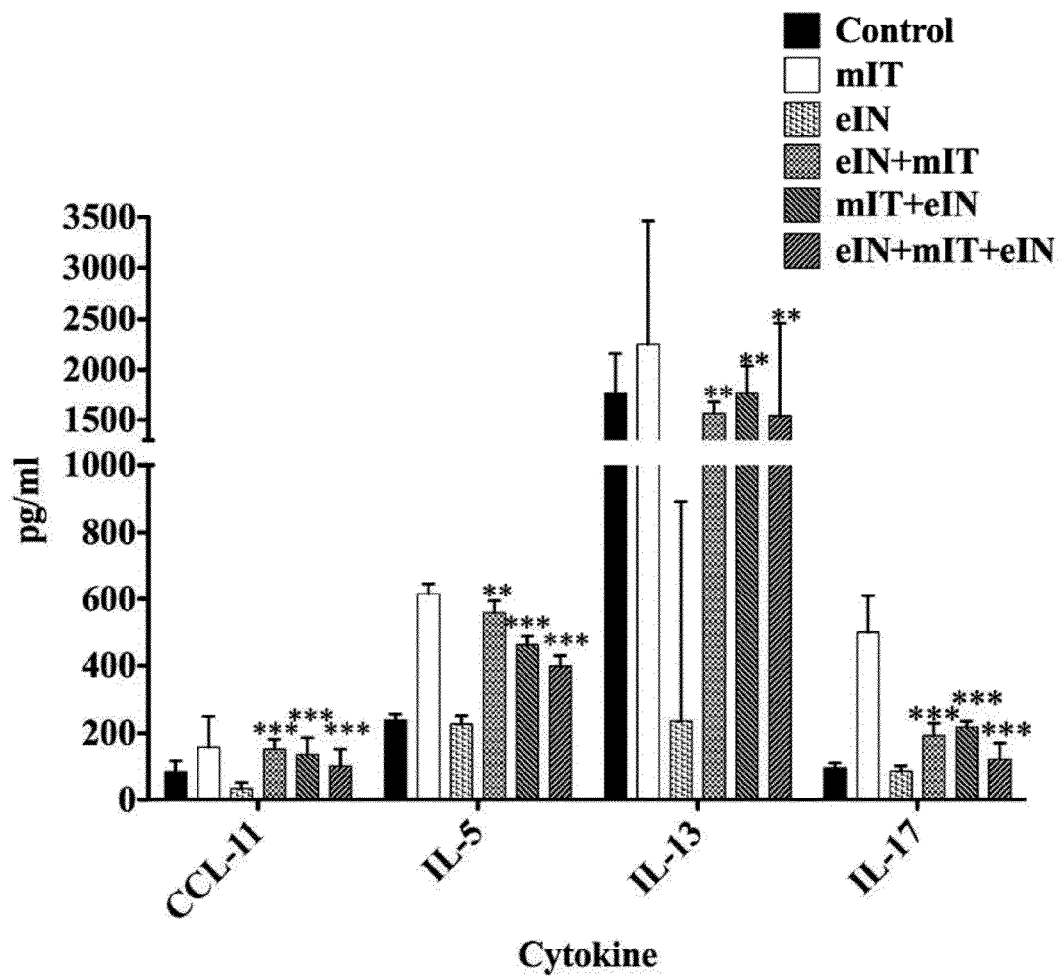
FIG. 9 illustrates inhibitory effect of CMP on lung protein extract. Lung protein extracts from different groups of mouse were assayed for the indicated cytokines. Data represent one of three independent experiments. Levels of CCL-11, IL-5, IL-13 and IL-17A/F levels in lung protein extracts from mouse from treatment groups were measured by Enzyme-linked immunosorbent assay (ELISA). Each result was expressed as the mean±S.D., n=4. , $P<0.01$, *, $P<0.001$.

Mite can induce allergic asthma in BALB/c mouse, through inducing an immune deviation from Th1 to Th2 (Stevens, W. H., et al., (1995) *Am J Respir Crit. Care Med,* 151: 1526-31). Recent studies have demonstrated that allergic airway inflammation is mediated by both Th2 cytokine (IL-13) and Th17 cytokine (IL-17A/F) in the BALB/c model of asthma (Mukherjee S, et al. (2011) *Am J Pathol* 179: 248-58). In concert with Th2 cells, Th17 cells are important during the development of AHR. In humans, increased expression of IL-17A/F occurs in the bronchial submucosa of patients with moderate-to-severe asthma (Doe C, et al. (2011) *Chest* 138: 1140-1147). To examine whether CMP could also reverse the Th1/Th2/Th17 bias, the levels of several cytokine in BALF were measured. Three groups, eIN+mIT, mIT+eIN, and eIN+mIT+eIN, had lower concentrations of CCL-11 than did the mIT group. IL-5 levels were also lower in mIT+eIN and eIN+mIT+eIN groups, as well as eIN+mIT group. eIN+ mIT, mIT+eIN, and eIN+mIT+eIN groups all had lower concentrations of IL-13 than did the mIT group (FIG. 9). The IL-17A/F levels in these groups were also much lower than that of the mIT group (FIG. 9). CMP groups decreased eotaxin, IL-5, and IL-13 in lung protein extract, indicating that CMP could lessen cytokine-mediated airway inflammation and affect eosinophil activation. Another interesting finding was that CMP decreased IL-17A/F in lung protein extracts. Thus, the connection between CMP and IL-17 regulation illustrated that CMP was an attractive therapeutic approach for pulmonary disease. These evidence indicated CMP as an alternative treatment to current anti-inflammation medications for pulmonary disease patients.

Example 8

Migration Inhibition of Tumor Cells by CMP

Migration Assay

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

All publication, patents and patent application are herein incorporated by reference in their entirety to the same extent as if each individual publication, patent or patent application was specifically and individually indicated to be incorporated by reference in its entirety.

```
                        SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: CMP
<220> FEATURE:
<221> NAME/KEY: PEPTIDE
<222> LOCATION: (1)..(10)

<400> SEQUENCE: 1

Asn Tyr Arg Trp Arg Cys Lys Asn Gln Asn
```

Cancer cell inhibition by CMP was performed in a 24-well Transwell chamber consisting of a cell culture insert (6.4 mm diameter, 8-1 µm pore polyethylene tetraphtalate membrane, [Becton Dickinson]) set in each well of a 24-well companion plate (Becton Dickinson). Briefly, $3 \times 10^4$ cancer cells were suspended and pretreated with 5 and 12.5 µM CMP for 30 min in a total volume of 200 µL. Cell suspensions were inoculated into the upper chamber of an insert, 5% fetal bovine serum (FBS) in medium as a chemoattractant was added to the plate well in the bottom chamber, and incubated for 18 hours in a humidified incubator at 37° C. with 5% $CO_2$. The non-migratory cells on the upper membrane surface were removed with a cotton swab, and the migratory cells attached to the lower membrane surface were fixed with 4% paraformaldehyde and stained with 0.2% crystal violet. The number of migrated cells was counted in four randomly selected high power fields under microscope. Data presented are representative of three individual wells.

Figure 10:
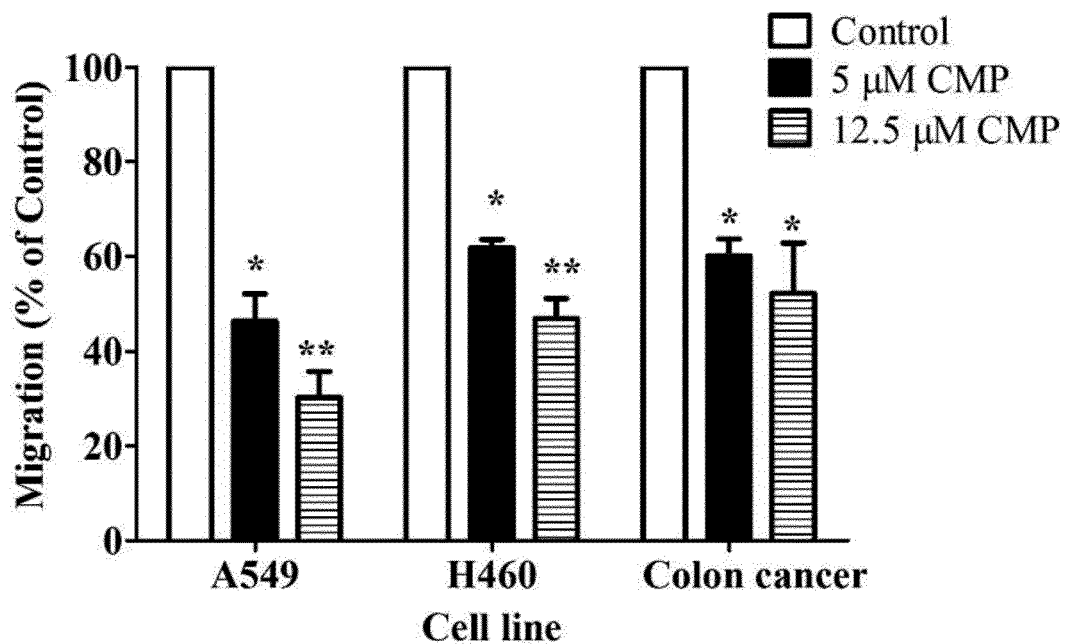
FIG. 10 illustrates Tumor migration inhibition by CMP. A549, H460 and mouse colon cancer cells were incubated with CMP at 37° C. for 30 min before adding to the top chamber of transwell membranes in 24-well dishes at a density of 2×10⁴ cells/well. Data represented the mean±S.E. of triplicate samples from a representative experiment. The experiment was repeated at least three times with similar results

GAGs such as HS and CS have been reported to attract growth factors highly involved in cell growth, development and matrix remodeling, so CMP was aroused an interest to block regulatory factors trapped on extracellular matrix and thus prevented cancer migratory activity. CMP was applied on human lung cancer A549 and H460 as well as mouse colon cancer cells to elucidate its tumor migration activity. Cells were pretreated with 5 or 12.5 µM CMP for 30 min and cell migration was examined by transwell assay. CMP at 5 µM could decrease 60% migration activity of A549 and mouse colon cancer, and decrease 50% of H460 at a concentration of 12.5 µM (FIG. 10).

What is claimed is:

1. A method for treating eosinophilia in a subject in need thereof by downregulating CCL-11 expression in the subject, comprising administering to the subject a pharmaceutically effective composition of a peptide consisting of SEQ ID NO: 1.

2. The method of claim 1, wherein administration is achieved by a route selected from inhalation, intranasal, aerosol, or intratracheal.

3. The method of claim 1, wherein the eosinophilia is associated with asthma, bronchitis, allergic bronchitis, bronchial asthma, emphysema, chronic obstructive pulmonary disease, or lung fibrosis.

4. The method of claim 1, wherein the composition reduces inflammation, leukocyte recruitment, chemokine levels or inflammatory cytokine levels in the subject.

5. The method of claim 4, wherein the leukocyte is macrophage, basophil, neutrophil, eosinophil or lymphocyte.

6. The method of claim 4, wherein the chemokine is CCL-26 or CXCL-12.

7. The method of claim 4, wherein the inflammatory cytokine is IL-1β, IL-4, IL-5, IL-6, IL-8, IL-13 or IL-18.

8. The method of claim 1, wherein the composition reduces severity of asthma attack, airway obstruction, bronchial spasms, airway hyperreactivity, histopathological inflammation score, goblet cells hyperplasia or IgE levels in the subject.

9. The method of claim 1, wherein the composition decreases airway resistance in the subject.

10. The method of claim 1, which further comprises administering an agent selected from the group consisting of steroids, anti-IgE antibodies, anti-IL-4 antibodies, anti-IL-5 antibodies, leukotriene inhibitors, lipoxygenase inhibitors, IL-13 antagonists, cytokine release inhibitors, anti-histamines and histamine release inhibitors.

11. The method of claim 1, wherein the subject is mammal.

* * * * *